United States Patent
Kensy et al.

(10) Patent No.: US 8,628,950 B2
(45) Date of Patent: Jan. 14, 2014

(54) PROCEDURE AND DEVICE FOR SEPARATING ADULT STEM CELLS FROM FATTY TISSUE

(75) Inventors: Arnd Kensy, Michendorf (DE); Konrad-Wenzel Winkler, Warin (DE)

(73) Assignee: Human Med AG, Schwerin (DE)

( * ) Notice: Subject to any disclaimer, the term of this patent is extended or adjusted under 35 U.S.C. 154(b) by 0 days.

(21) Appl. No.: 13/246,275

(22) Filed: Sep. 27, 2011

(65) Prior Publication Data

US 2012/0100611 A1    Apr. 26, 2012

Related U.S. Application Data

(60) Provisional application No. 61/405,246, filed on Oct. 21, 2010.

(30) Foreign Application Priority Data

Oct. 20, 2010  (DE) .......................... 10 2010 049 203
Aug. 2, 2011   (DE) .......................... 10 2011 080 218

(51) Int. Cl.
  *C12M 1/00*    (2006.01)
  *C12N 5/074*   (2010.01)

(52) U.S. Cl.
  USPC ................... 435/286.6; 435/283.1; 435/378; 422/527

(58) Field of Classification Search
  USPC ................... 435/283.1, 378, 286.6; 422/527
  See application file for complete search history.

(56) References Cited

U.S. PATENT DOCUMENTS

2012/0276629 A1 * 11/2012 Lee .............................. 435/381

FOREIGN PATENT DOCUMENTS

| DE | 102010001292 A1 | 7/2011 |
| JP | 2010104918 A | 5/2010 |
| WO | 2007/009036 A2 | 1/2007 |
| WO | 2008/143570 A1 | 11/2008 |
| WO | 2010/045389 A1 | 4/2010 |
| WO | 2010/073808 A1 | 7/2010 |
| WO | 2011/062313 A1 | 5/2011 |

OTHER PUBLICATIONS

Bunnel B. A. et al, "Adipose-derived stem cells: Isolation, expansion and differentiation", Methods: A companion to methods in enzymology, Academic Press Inc., New York, Bd. 45, Nr. 2, 1. Jun. 2008.
German Search Reported dated Aug. 26, 2011.

* cited by examiner

*Primary Examiner* — David A Reifsnyder
(74) *Attorney, Agent, or Firm* — Norris McLaughlin & Marcus PA

(57) ABSTRACT

The invention relates to a method for separating adult stem cells from fatty tissue, wherein the fatty tissue is mixed with a fluid and the stem cells are subsequently separated. The fatty tissue with fat cells and adult stem cells is exposed to a fluid jet (38) having a pressure adjusted such that the adult stem cells are separated from the fat cells and the adult stem cells are separated from the fat cell-stem cell-fluid mixture. A container (12) is provided for receiving fatty tissue removed from a biological structure, which includes fat cells (62) and adult stem cells (64), wherein the container (12) has a feed device (28) for a pressurized fluid and the feed device (28) includes an outlet the arrangement (30) for the fluid which is introduced or can be introduced into the fatty tissue.

5 Claims, 2 Drawing Sheets

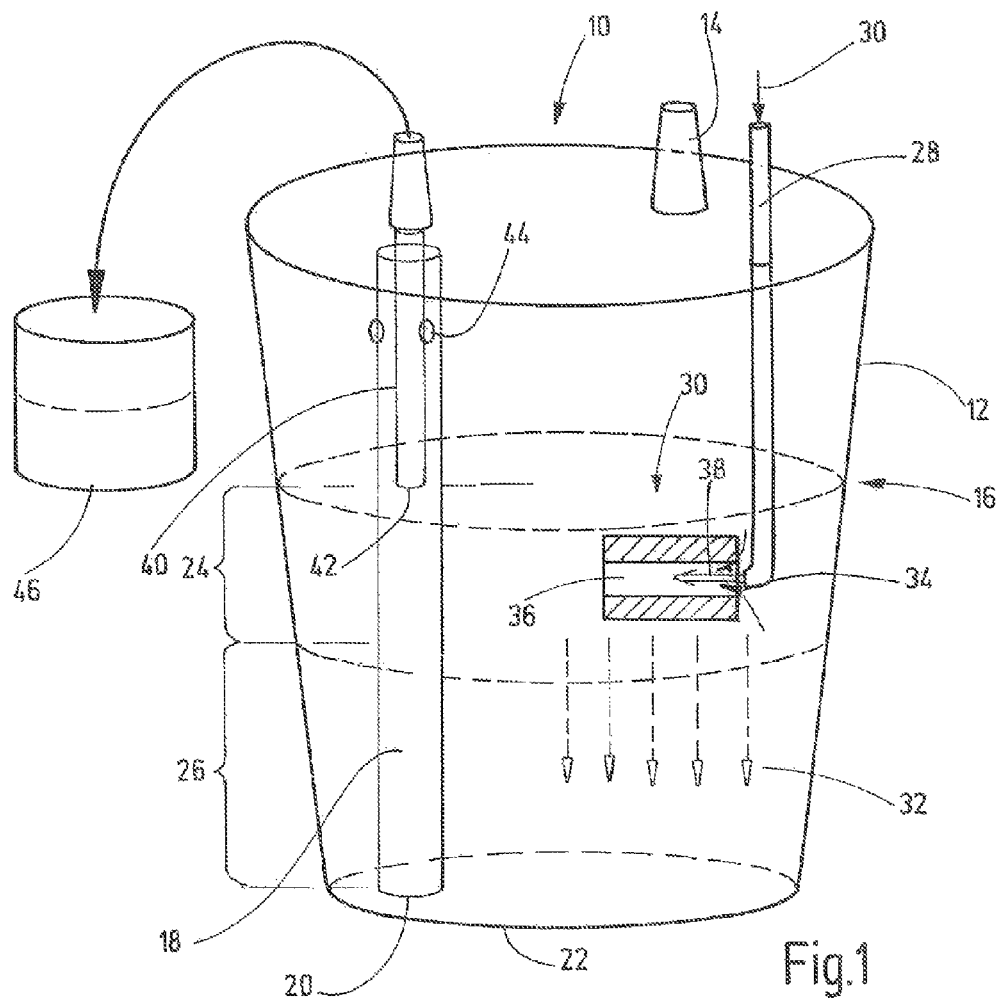
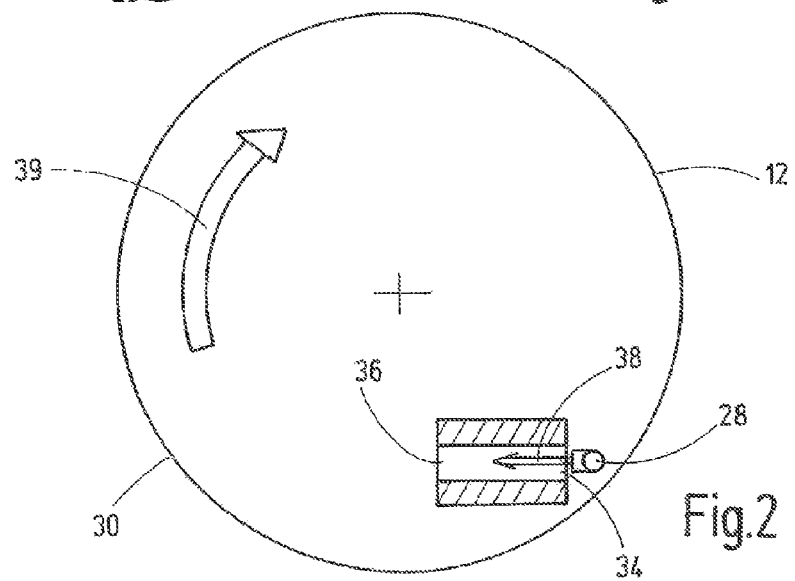

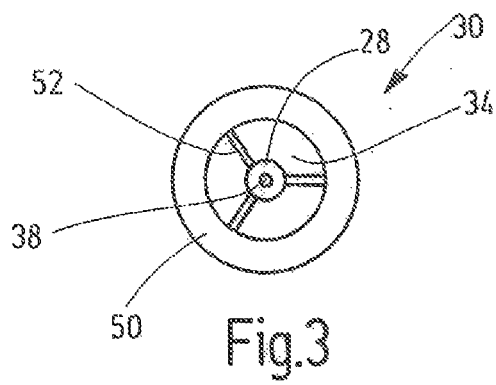
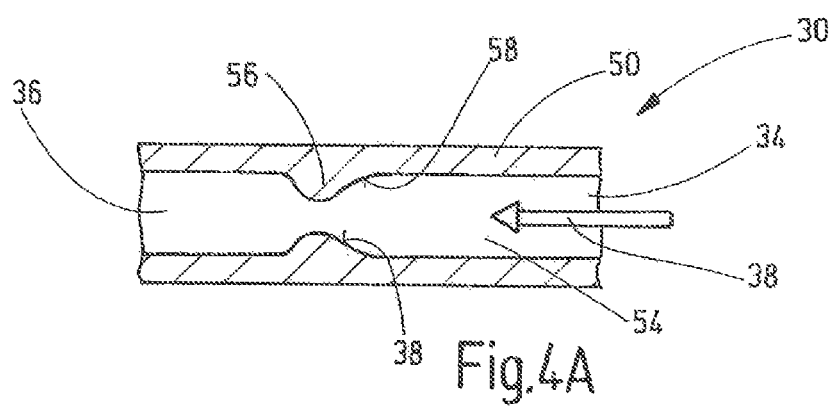
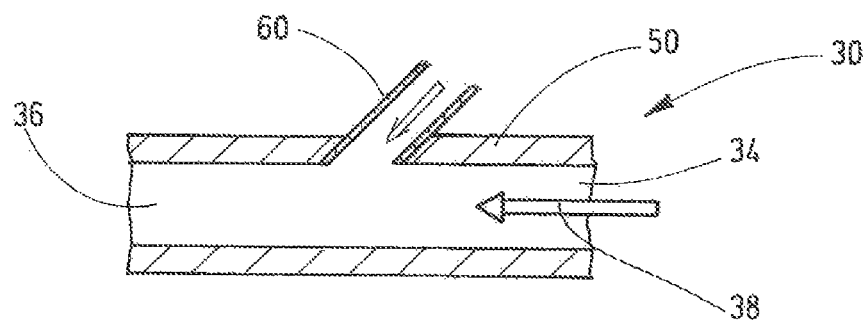
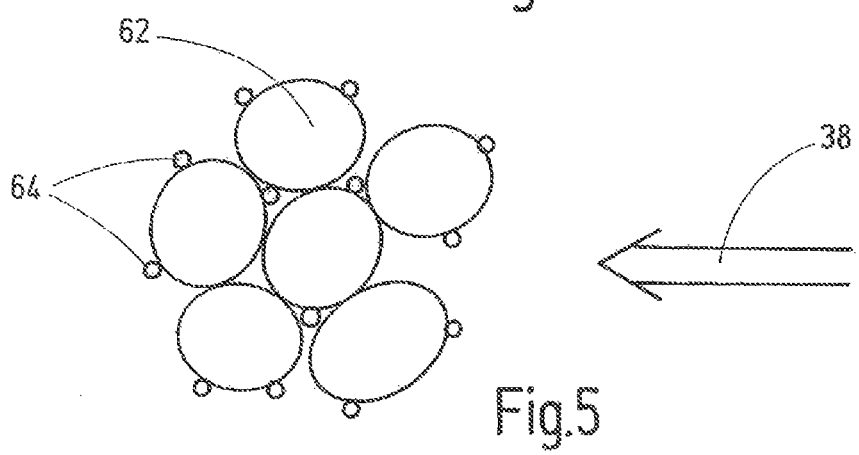

PROCEDURE AND DEVICE FOR SEPARATING ADULT STEM CELLS FROM FATTY TISSUE

The invention relates to a method and an apparatus for separating adult stem cells from fatty tissue It is known, for example in human medicine, to obtain fatty tissue from biological structures. As is generally known, fatty tissue is suctioned off with suitable suctioning devices and collected in so-called fatty tissue cell collectors.

It is known that the obtained fatty tissue also includes stem cells in addition to fat cells. Stem cells are body cells which can differentiate themselves into different cell types or tissues. The stem cells present in fatty tissue are so-called adult stem cells.

It is known, for example from WO 2010/073808 A1, to obtain such adult stem cells from fatty tissue by adding to the fatty tissue a fluid containing an enzyme and to thereafter centrifuge the mixture in a container. The stem cells are then detached from the fatty cells, so that they can be separately collected.

It is the object of the invention to provide a method and an apparatus of the generic type, with which adult stem cells can be easily separated from fatty tissue.

According to the invention, the fatty tissue is exposed to a fluid jet of a suitable pressure selected so that the adult stem cells can be separated from the fat cells. The adult stem cells are mechanically separated from the fat cells and subsequently segregated from the fat cells. The stem cells can thereby be washed out of from the fatty tissue. The adult stem cells are segregated from the fat cells by applying a pressurized fluid jet. In the mixture which contains fat cells, adult stem cells and fluid produced by the fluid, the adult stem cells sink due to their greater density, whereas the fat cells float due to their smaller density relative to the employed fluid. The fat cells are thereby segregated from the adult stem cells through sink fraction. The adult stem cells can then be separated, for example through suctioning and the like, and collected. Preferably, the stem cells can subsequently be filtered out from the stem cell-fluid mixture.

The object is furthermore solved by an apparatus for separating adult stem cells from fatty tissue, which includes a container for receiving fatty tissue removed from a biological structure, wherein the container has a feed device for a pressurized fluid, with the feed device having a outlet arrangement for the fluid which is introduced or can be introduced into the fatty tissue. In this way, the fatty tissue which includes the adult stem cells and the fat cells can advantageously be exposed to a fluid jet. The fluid jet causes, at a suitable pressure, separation of the adult stem cells from the fat cells. The fluid jet also establishes a flow direction of the entire mixture inside the container, so that new fat cells connected with adult stem cells always reach the exposure zone of the fluid jet. In this way, the adult stem cells can be very effectively separated from fat cells. The adult stem cells sink within the mixture due to the different density and can be separately removed.

In a preferred embodiment of the invention, the outlet arrangement includes a hollow body with an inlet opening and an outlet opening, wherein the fluid jet passes through the outlet opening. Advantageously, the outlet arrangement is then at the same time also a defined mixing chamber for the fatty tissue with the introduced fluid. The hollow body is preferably formed as a hollow cylinder. In this way, on one hand, a defined flow in the container with the fatty tissue-fluid mixture can be generated by the fluid jet and, on the other hand, a space can be created in which the adult stem cells are washed off from the fat cells. The effect of the fluid jet on the fatty tissue can be controlled via the shape and size of the hollow body, in particular the hollow cylinder.

In another preferred embodiment of the invention, the outlet arrangement has flow surfaces. The fluid jet can flow against the flow surfaces and can thereby be deflected. In this way, the fatty tissue can advantageously be swirled inside the outlet arrangement, so that the adult stem cells can be more effectively washed out from the fat cells.

Furthermore, in a preferred embodiment of the invention, the outlet arrangement is in form of a nozzle, in particular a Venturi nozzle. In this way, the fatty tissue surrounding the outlet arrangement is simultaneously suctioned into the outlet arrangement when the fluid jet is introduced into the outlet arrangement. Additional measures for introducing the fatty tissue into the outlet arrangement, which simultaneously forms the processing chamber for washing out the stem cells, are not required. The entire apparatus for separating the adult stem cells can thus have a simple and compact structure.

Additional preferred embodiments of the invention are recited as further features in the dependent claims.

An exemplary embodiment of the invention will now be described in more detail with reference to the appended drawings, which show in:

FIG. 1 a schematic side view of the apparatus according to the invention for separating adult stem cells;

FIG. 2 a schematic top view on the apparatus;

FIG. 3 a schematic cross-sectional view through the outlet arrangement;

FIG. 4 schematic diagrams of several possible embodiments of the outlet arrangement; and FIG. 5 a schematic view of fat cells.

FIG. 1 shows schematically an apparatus 10 for separating adult stem cells from fatty tissue. The apparatus 10 includes a container 12 into which fatty tissue removed from an unillustrated biological structure is introduced via a depicted connection 14. The fatty tissue is typically removed from the biological structure by a so-called waterjet surgical procedure and is in form of a fatty tissue-fluid mixture. A level, indicated here with 16, is adjusted inside the container 12 commensurate with the introduced quantity of the fatty tissue-fluid mixture. A tube 18 connected with an unillustrated vacuum source is introduced inside the container 12, with the mouth 20 of the tube 18 located just above a bottom 22 of the container 12.

Due to the density of the fat cells, a layer 24 of fat cells of the fatty tissue and a layer 26 of the fluid are formed. The fat cells in the layer 24 are mixed with adult stem cells just as they are obtained from the biological structure. In general, the much smaller dimensioned adult stem cells dock on the surface of the larger fat cells and adhere to the larger fat cells (FIG. 5).

The apparatus 10 further includes a feed device 28 for a pressurized fluid, for example water. The fluid flow towards the container 12 can be started, interrupted, attenuated or switched off by way of an unillustrated switching device. The feed device includes a schematically indicated outlet arrangement 30 through which the fluid jet is introduced into the layer 24 containing the fat cells. The outlet arrangement is connected with the feed device 28 via unillustrated connection means, thereby producing an integrated unit.

The fluid jet has a suitable pressure, for example between 2 and 10 bar, in particular between 3 and 4 bar, so that the adult stem cells are separated from the fat cells. These are quasi washed off by the jet effect of the fluid jet. The separated stem cells sink inside the layer 26 towards the bottom 22 due to their greater density—as indicated here by the arrows 32.

The outlet arrangement 30 is formed as a hollow body, for example as a hollow cylinder, and has an inlet opening 34 and an outlet opening 36. When the fluid flow is introduced, here indicated with 38, the fat cells are drawn into the outlet arrangement 30 through the inlet opening 34, where they meet the fluid jet 38. The fat cells are hereby carried along and the adult stem cells are washed of the fat cells, as already described above. The fluid jet 38 simultaneously produces an oriented flow within the entire layer 24 of the fat cells.

As illustrated in the schematic top view of FIG. 2, the outlet arrangement 30 is located in a radially outer region of the container 12. This produces a basic flow within the layer 24, which is indicated here with the arrow 39. As a result, the fat cells are mixed and/or moved within the layer 24 and reach after a certain time the region of the outlet arrangement 30. In this way, the adult stem cells can be almost completely washed out from the fat cells.

The adult stem cells sink, as already explained, to the bottom 22 of the container 12, where there are suctioned off together with the fluid through the tube 18. For this purpose, a suction fitting 40 is arranged inside the tube 18, with the suction mouth 42 determining the height of the level 16. The pressure is equalized with the region above the level 16 inside the container 12 by way of openings 44 disposed in the tube 18. The adult stem cells which enter the tube 18 through the opening 20 are suctioned off together with the fluid. The so obtained fluid/stem cell mixture is transported to another schematically indicated container 46, where the stem cells can then be filtered from the fluid.

To increase the effectiveness, the flow channel of the outlet arrangement 30 may have differently contoured flow surfaces. These may, for example, form at least one nozzle. Moreover, diverting surfaces may be provided which improve the flow of the fluid jet 38 against the fatty tissue. In this way, the adult stem cells can be better washed off from the fat cells.

FIG. 3 shows a schematic top view onto the outlet arrangement 30. As can be seen, the outlet arrangement 30 is comprised of a hollow cylinder 50, with the feed device 28 extending to the center of the hollow cylinder 50. The feed device 28 can be attached to the hollow cylinder 50 by way of schematically indicated ribs 52. The diagram of FIG. 3 shows a view into the outlet arrangement 30 from the direction of the outlet opening 36. The inlet opening 34 is formed by the residual annular gap remaining between the outlet arrangement 28 and the hollow cylinder 50. The fatty tissue with the fat cells and the adult stem cells reaches the outlet arrangement 30 via this inlet opening 34. The fluid jet 38 enters the outlet arrangement 30 at the center, so that the fatty tissue is symmetrically carried along in the outlet arrangement 30. The fluid jet 38 then hits the fatty tissue inside the outlet opening 30 and washes off adult stem cells adhering to the fat cells.

FIG. 4A shows a schematic cross-sectional diagram through a modified embodiment of the outlet arrangement 30. As can be seen, the hollow cylinder 50 forms a constriction 56 in its flow space 54. Flow surfaces 58 are thereby formed, against which the fluid jet 38 and the entrained fatty tissue are flowing. Vortices are produced on the flow surfaces 58, potentially improving the wash-out of the adult stem cells adhering to the fat cells by the fluid jet 38.

FIG. 4B shows another modified embodiment of an outlet arrangement 30. In this embodiment, a bypass 60 with an opening to the fatty tissue inside the container 12 extends into the hollow cylinder 50. When the fluid jet 38 enters the interior space of the hollow cylinder 50, the bypass 60 forms a so-called Venturi nozzle, i.e., the fluid jet 38 carries along through the bypass 60 an additional volume quantity of fatty tissue. This can increase the effectiveness of the outlet arrangement 30 when washing out adult stem cells adhering to the fat cells.

FIG. 5 shows in a simplified schematic diagram a collection of fat cells 62, with adult stem cells 64 adhering to the surface of the fat cells 62. The stem cells 64 are mechanically washed off from the surface of the fat cells 62 when the schematically illustrated fluid jet 38 impinges. The stem cells 64 then no longer adhere to the fat cells 62, so that the stem cells 64 sink towards the bottom inside the container due to their greater density (FIG. 1).

The invention claimed is:

1. Apparatus for separating adult stem cells from fatty tissue, comprising a container (12) for receiving fatty tissue removed from a biological structure, the fatty tissue comprising fat cells (62) and adult stem cells (64), wherein the container (12) has a feed device (28) for a pressurized fluid and the feed device (28) comprises an outlet arrangement (30) for the pressurized fluid, wherein the outlet arrangement (30) is introduced or is structured for introduction into the fatty tissue, the pressure of a fluid of the pressurized fluid jet being adjustable such that the adult stem cells may be separated from the fat cells and the adult stem cells may be separated from the fat cell-stem cell-fluid mixture.

2. Apparatus according to claim 1, wherein the outlet arrangement (30) comprises a hollow body with an inlet opening (34) and an outlet opening (36), wherein the fluid jet (38) passes through the outlet arrangement (30).

3. Apparatus according to claim 2, wherein the hollow body is constructed as a hollow cylinder (50).

4. Apparatus according to claim 3, wherein the hollow cylinder (50) comprises flow surfaces (58).

5. Apparatus according to claim 1, wherein the outlet arrangement (30) comprise a Venturi nozzle.

* * * * *